United States Patent [19]

Galloway et al.

[11] Patent Number: 5,403,551
[45] Date of Patent: Apr. 4, 1995

[54] ASSAYING DEVICE AND CONTAINER FOR IN FIELD ANALYSIS OF A SPECIMEN AND LATER SHIPMENT OF THE UNADULTERATED SPECIMEN

[75] Inventors: R. Keith Galloway, New Britan, Pa.; Steven S. Bachand, Laguna Niguel; Stephen K. Schultheis, Laguna Hills, both of Calif.

[73] Assignee: Roche Diagnostic Systems, Inc., Branchburg, N.J.

[21] Appl. No.: 122,227

[22] Filed: Sep. 16, 1993

[51] Int. Cl.$^6$ ............................................. G01N 21/03
[52] U.S. Cl. .................................... 422/58; 422/56; 422/61; 422/100; 422/101; 422/102; 128/760; 436/165; 436/169
[58] Field of Search ................... 128/760, 771; 422/56, 422/58, 61, 100–102; 436/162, 165, 169, 180, 810, 816, 901

[56] References Cited

U.S. PATENT DOCUMENTS

| | | | |
|---|---|---|---|
| 3,832,134 | 8/1974 | Sohn | 436/162 |
| 3,849,256 | 11/1974 | Linder | 422/102 X |
| 3,980,436 | 9/1976 | Greenfield et al. | 422/61 X |
| 4,070,249 | 1/1978 | Janin et al. | 422/102 X |
| 4,385,115 | 5/1983 | de Zabala et al. | 435/300 X |
| 4,435,504 | 3/1984 | Zuk et al. | 436/162 X |
| 4,454,235 | 6/1984 | Johnson | 422/102 X |
| 4,624,929 | 11/1986 | Ullman | 436/162 X |
| 4,865,813 | 9/1989 | Leon | 436/165 X |
| 4,885,253 | 12/1989 | Kralovic | 422/101 |
| 5,119,830 | 6/1992 | Davis | 422/102 X |
| 5,149,505 | 9/1992 | English et al. | 422/102 X |
| 5,186,897 | 2/1993 | Eason et al. | 436/180 X |

Primary Examiner—James C. Housel
Assistant Examiner—Arlen Soderquist
Attorney, Agent, or Firm—Walter A. Hackler

[57] ABSTRACT

An assaying device is provided for both collecting and analyzing a sample which includes a container and an opening for collecting the sample in a chamber for storing the sample. A cap is provided for sealing the container opening and at least one assay system is attached to the container for chemically analyzing the sample. A channel is provided for enabling a portion of the sample to enter the assay system upon a change of orientation of the container. A tamper-proof device is provided through the use of a releasable seal which permits the sample to enter the assay system only when desired.

23 Claims, 3 Drawing Sheets

ASSAYING DEVICE AND CONTAINER FOR IN FIELD ANALYSIS OF A SPECIMEN AND LATER SHIPMENT OF THE UNADULTERATED SPECIMEN

The present invention generally relates to assaying devices and is particularly suitable for field devices for determining the presence of chemical constituents in a great number of areas. In today's present earth conscious society it has become very important to detect the presence of unwanted or undesirable compounds which may exist in the environment or in animals.

As an example, it is important to be able to assay on a field basis the presence of water pollutants which may include any number of industrial chemicals, as well as pesticides. In addition, body fluids of animals are often tested to determine pollutants which may range from pesticides to drugs.

Regarding the latter, the increased availability and use of drugs by the general population has caused employers, government agencies, sports groups, and other organizations to utilize drug screenings as both conditions of employment and maintenance of safety in the work place.

Because of the large numbers involved, the collection and testing of body fluid samples, such as urine, must be simple and cost-effective.

In addition to this, it is also a requirement that the samples taken be guaranteed as to their integrity; i.e., adulteration of the samples must be prevented in order to guarantee accurate test results. This requirement for integrity, of course, may raise the question of invasion of privacy if a visual observation of the collection step is required.

Most importantly, the onset of AIDS (Acquired Immune Deficiency Syndrome) has significantly increased the health risks associated with the handling of body fluids. Heretofore utilized devices for the collection and taking of body fluids, such as urine, for example, have involved separate steps. The first step was the collection of the sample and thereafter a number of steps which require transfer of the urine sample to an analysis system or device was needed. Naturally, this multiple step procedure has necessitated the manual handling of the sample through the use of pipettes, syringes or other devices. The use of these transfer devices inevitably causes a few spills which may result in contamination to the analyst or his/her surroundings.

In addition, another major drawback to conventional collection and testing systems is the fact that the sample tested must be removed from the collection device, and as a result, there is the possibility for a mix-up or misidentification of the sample drawn from the collection cup. This mix-up of samples can prove embarrassing and often results in detrimental results in regard to the employment and clinical record of the person being tested.

Inasmuch as typical drug screening tests are performed only for the purpose of quickly identifying on a qualitative basis the presence of drugs in a body fluid, such as urine, with a complete analysis of the sample being performed only if the screening results are positive, it is of utmost importance that the results of drug screening performed on the body fluid sample being positively identified with the sample in order to ensure proper one-to-one correlation of the sample with the person being tested. This, of course, is placed in jeopardy once a sample is transferred from a collection cup to another separate analysis device or system.

The present invention is directed to an assaying device, suitable for in-field testing for chemical constituents in fluids for any number of applications as hereinabove set forth, that requires no specimen handling after the collection step. Hence, not only is the risk of contamination virtually eliminated, but since the collection and analysis are performed by a single device, no misidentification of the sample is possible.

In the case of assaying body fluids for drugs, a measured specimen volume, specimen storage and tamper-evident access to the specimen after a test are provided by the present invention. Further, a multiplicity of drug analyses may be performed simultaneously with the device hereinbelow described.

SUMMARY OF THE INVENTION

An assaying device, in accordance with the present invention, for both collecting and analyzing samples, generally includes a container having an opening for collection of a sample and a chamber for storing the collected sample. A cap provides a means for sealing the container opening and assay means, attached to the container, is provided for chemically analyzing the sample.

Importantly, means are provided for introducing a portion of the sample within the chamber into the assay means when the cap is in the position sealing the container opening. In this manner, there is no requirement for removing the sample from the assaying device in order to conduct a chemical analysis.

In this regard, the apparatus of the present invention totally eliminates the transfer of a sample from the device in order to conduct chemical analysis as is the case with all prior art devices. As hereinabove noted, this has a significant advantage in terms of both laboratory safety and time savings.

Of particular importance, one embodiment of the present invention particularly suitable for drug screening of body fluids includes means for preventing premature or inadvertent entry of the sample into the assay means. In addition, since the body fluid sample never leaves the device, if a positive test for a drug is indicated, the entire device may be removed or shipped to another area or laboratory in order to complete a quantitative and confirmatory analysis of the body fluid.

More particularly, in accordance with the present invention, the assay means may include chromatograph means positioned on the container for enabling direct visual observation thereof. Thus, no additional step is necessary for effecting a drug screening analysis of body fluid.

As hereinabove noted, the drug screening device, in accordance with the present invention, may further include means for preventing body fluid to enter the chromatograph means during collection of the body fluid. This is important in order to prevent a premature or inadvertent activation of the drug screening analysis; and further, the possibility of adulteration of the body fluid by the person being tested is substantially, if not totally, eliminated.

Channel means may be provided for enabling a portion of the body fluid to enter the chromatograph means on a change of orientation in the container. Particularly, the means for preventing body fluid from entering the channel means during collection of the body fluid may be configured for enabling body fluid to enter the channel means only when the container is inverted.

Preferably, in accordance with the present invention, means are provided for releasably sealing the channel means in order to prevent body fluid from prematurely or inadvertently entering the channel means.

The chromatograph means may be permanently attached to the exterior of the container side wall, and the channel means includes a plenum and means defining at least one bore in the container side wall for conveying body fluid to the chromatograph means.

The chromatograph means may comprise a plurality of separated thin layer chromatograph strips with each strip comprising means for chemically analyzing the body fluid for a different specific analyte.

More particularly, the chromatograph means may include wick means for evenly distributing the body fluid to each of the plurality of separated chromatograph strips and the chromatograph strips may be disposed in a generally parallel relationship with one another and a longitudinal axis of the container. The wick means may be disposed at one end of each chromatograph strip and the chromatograph means may further include a pad in order to receive fluid passing through the strips.

BRIEF DESCRIPTION OF THE DRAWINGS

The advantages and features of the present invention will be better understood by the following description when considered in conjunction with the accompanying drawings in which.

DETAILED DESCRIPTION

Figures 1, 2:
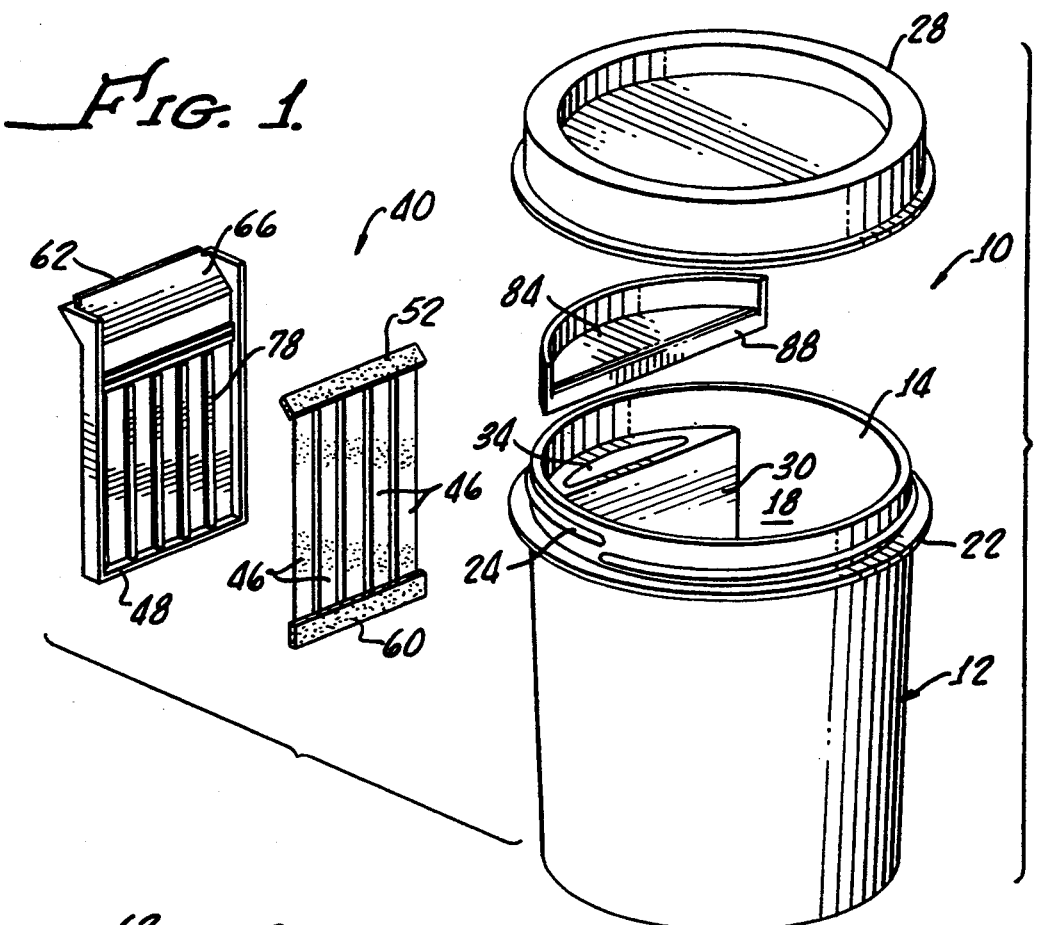
FIG. 1 is an exploded perspective view of the drug screening device in accordance with the present invention generally showing a container, cap, and assaying means.
FIG. 2 is another exploded perspective view of the present invention more clearly showing one embodiment of a molded housing for supporting chromatograph strips.

Turning now to FIGS. 1 and 2, there is shown an assaying device 10, in accordance with the present invention, for both collecting and analyzing a sample such as, for example, a body fluid (not shown). The device generally includes a container 12 having an opening 14 which provides a means for collecting the body fluid and a chamber 18 which provides a means for storing the collected body fluid.

The container 12 may be formed, or molded, from any suitable material, such as plastic, and may include a circumferential rib 22 for providing rigidity to the container 12 and screw threads 24 formed into the container proximate the opening 14 are sized for accepting a cap 28. As hereinafter described, the cap 28, when screwed onto the threads 24, provides a means for sealing the opening 14. For drug screening, a typical container 12 may have a capacity of between about 100 to about 120 ml; however the present invention is not intended to be limited to this size or capacity.

Figure 3:
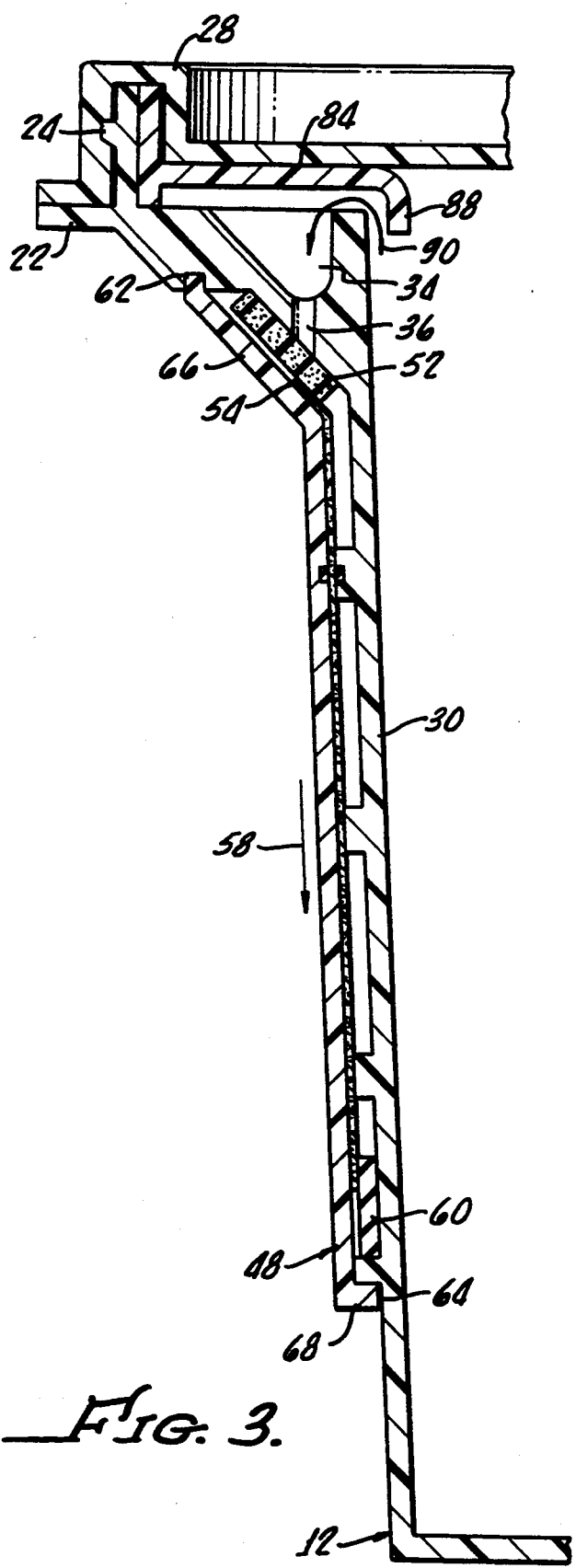
FIG. 3 is a cross-sectional view of the chromatograph means in place along a side wall of the container.

On an inside wall 30 of the container 12, there is formed a plenum, or reservoir, 34 and a plurality of bores 36 through the container wall, as shown in FIGS. 2 and 3. As hereinafter described in greater detail, the plenum 34 and bores 36 provide a means for conveying body fluid to assay means 40 which provides for chemically analyzing the sample. In the case of drug testing, the sample may be a body fluid, such as urine, and the assay means may be a chromatograph system as hereinafter described. It should be apparent that the assay system 40 utilized must have activity for testing one or more related components of the sample.

While only one reservoir 34 is shown, it should be appreciated that a plurality of reservoirs may be utilized, each communicating with a bore 36.

Generally, the chromatograph means 40 includes a housing 42 molded into a flat side 44 of the container 12. A plurality of latex/antibody strips 46 and a cover 48 for the latex/antibody strips 46 may be of any conventional thin layer chromatograph strips.

Each of the strips may be specific to a different analyte, thereby enabling up to five analyte specific tests to be run concurrently on the body fluid. For example, the test may be for THC—COOH, Benzoylecgonine, Morphine, Amphetamine/Methamphetamine, and Phencyclidine.

It should be appreciated that any number of concurrent analyte specific tests may be performed with the device 10 of the present invention. While five strips are shown, a greater or smaller number of individual strips may be utilized, depending upon the desired number of tests to be run upon the body fluid. When assembled, as shown in FIG. 3, a wick material 52, disposed on one end 54 of each strip 46, provides a means for distributing the body fluid to each of the plurality of thin layer chromatograph strips 46 from the bores 36 when the container 12 is inverted as will be hereinafter discussed in greater detail.

When introduced into the end 54 of each strip 46 by the wick material 52, the body fluid advances through capillary action along the strip 46 to another end 56 of each strip 46 (see arrow 58 in FIG. 3), at which point it is absorbed by a pad 60. Seals 62, 64 on the top 66 and bottom 68 of a cover 48 prevent the escape of any body fluid from the chromatograph means 40. The bottom seal 64 may not be necessary depending on the absorbency of the pad 60.

The cover 48 may be permanently fixed to the container, thereby ensuring that the results of chemical analysis remain with the container 12, and if the cap 28 and threads 24 are made in a conventional manner preventing an easy removal of the cap, the remaining body fluid within the chamber 18 is permanently attached to the chemical analysis record provided by the chromatograph means 40. In this regard, the cover 48 may have a transparent portion 70 to enable visual observation of the chromatograph strips 46 therethrough.

Figure 5:
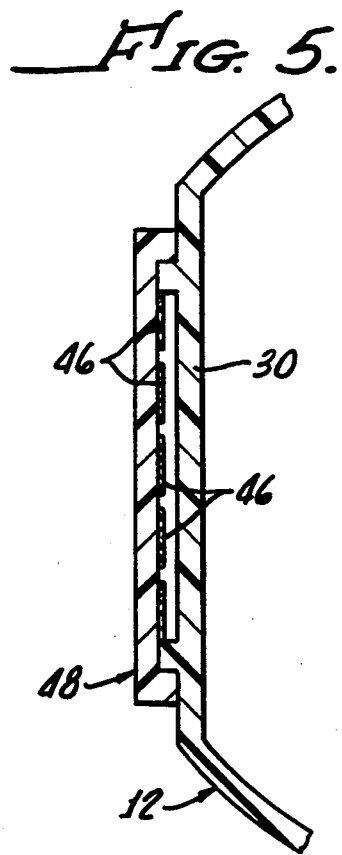
FIG. 5 is a cross-sectional view of another embodiment of the present invention, as shown in FIG. 2, showing a plurality of strips without spacers.

As shown in FIGS. 1 and 5, the plurality of strips 46 may be separated from one another by affixing the end 54 to the wick in a spaced apart relationship, and the ends 56 to the pad 60 in a spaced apart relationship. Thereafter, sealing of the cover 48 to the container 12 maintains sufficient tension in the strips 46 to prevent contact with one another.

Figure 4:
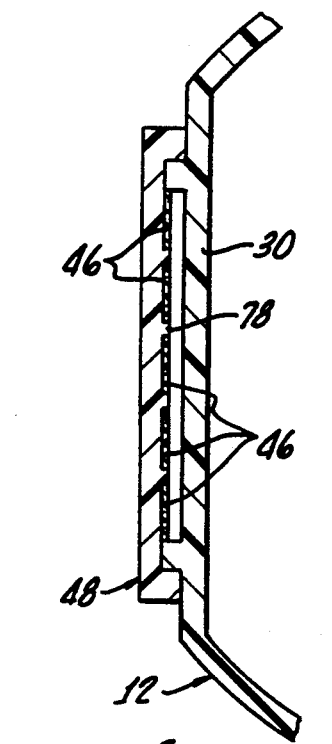
FIG. 4 is a partial view of one embodiment, as shown in FIG. 1, of the present invention, in which spacers may be provided for ensuring separation of the chromatograph strips.

Alternatively, as shown in FIG. 4, a plurality of spaced apart longitudinal ribs 78 may be disposed on the bars before positioning of the strips 46 and maintaining separation therebetween.

It should be appreciated that there should be minimum contact between the strips 46 and any surface, in order to prevent microhydrolic problems, such as channeling along an interface between the ribs 78 and the strips 46, which may otherwise compete with the capillary action of the fluid passing from one end 54 to another end 56 of each strip 46, thereby interfering with the chemical tests occurring during the movement of the body fluid along the strips 46. It has been found that with a minimum or no support of the strips 46, except by their ends 54, 56, the strips 46 may be disposed generally along the longitudinal axis 80 of the cup 12.

As shown in FIG. 1, an inner cap 84 may be affixed within the chamber 18 over the plenum 34 by gluing or the like which provides a means for preventing body fluid from entering the chromatograph means 40 during collection of the body fluid.

Figure 6:
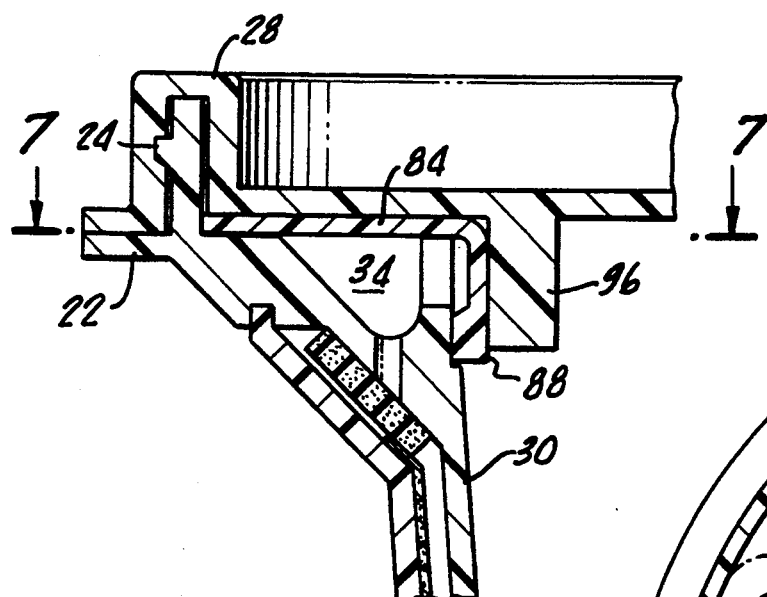
FIG. 6 is an enlarged cross-section view showing access to the chromatograph strips being sealed.
Figure 8:
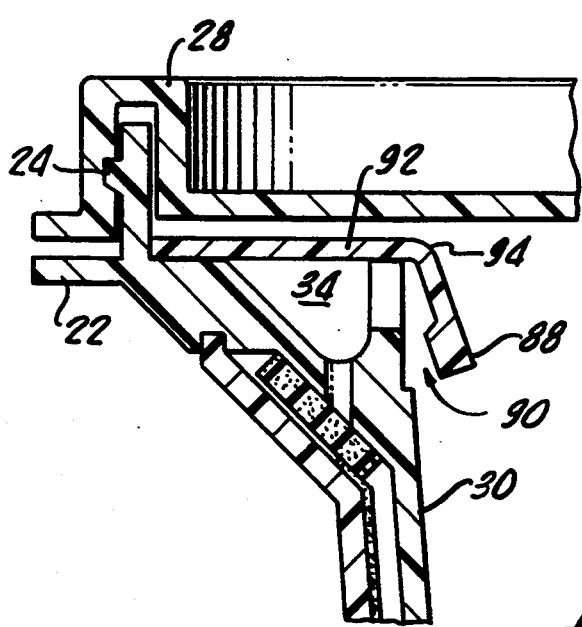
FIG. 8 is a view similar to FIG. 6 showing the flap in an open position.

As best shown in FIGS. 6 and 8, the inner cap 84 includes a downwardly depending flap 88 which establishes a flow path indicated by an arrow 90 (FIG. 8) for body fluid and therefore provides a means for introducing a portion of the body fluid within the chamber 18 into the chromatograph means 40 via the plenum 34 and bore 36 when the cap 28 is in the position of sealing container 12 and the container is tipped, or inverted.

The inner cap 84 provides an important function in substantially reducing or eliminating the possibility of adulteration of the body fluid by a person being tested. The inner cap 84 provides a visual block of the plenum and prevents downwardly projected body fluid, collected by the chamber 18, from directly entering the plenum 34. It is only when the container 12 is inverted that body fluid is able to flow along the flow path 90 under the inner cap 84 and into the plenum 34.

Once inverted, the plenum is filled by the body fluid and the amount of fluid in the plenum is sufficient to wet the strips 46 as it is distributed by the wick 52. Thus, the plenum and the wick provide a means for eliminating the flooding of the strips 46.

The cap 84 may be formed of any suitable plastic material or the like with an unsupported shape, as shown in FIG. 8, having a planar portion 92 covering the reservoir with the flap 88 molded thereto and pivotable about an arcuate joining portion 94.

Figure 7:
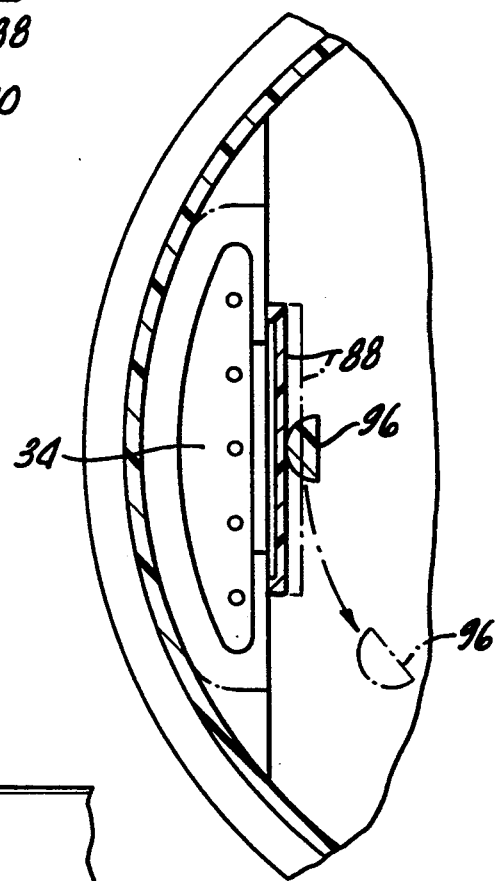
FIG. 7 is a view taken along line 7—7 of FIG. 6 (shown in cross-section) of a cap depending member urging a flap to a sealing position (solid lines) and an open position (broken lines)

As hereinbefore discussed, the cap 28 is sealably attached to the container 12 by means of threads 24 which are configured for enabling the cap to sealably engage the container 12 at both a first angular position shown in solid line in FIG. 7, in which a depending member 96 forces the depending flap 88 into a closed and sealed position against the inside wall, as shown in FIG. 6, to a second position, as shown in broken line in FIG. 7, which displaces the depending member 96 away from the depending flap 88, thus allowing the initial resiliency of the inner cap 84 to assume the free position shown in FIG. 8, which establishes the flow plan 90, as hereinabove mentioned.

Thus by rotation of the cap 28 with respect to the container, access to the reservoir by the sample in the container is controlled without breaking the integrity of the seal between the cap 28 and the container 12.

Although there has been hereinabove described an assaying device in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. An assaying device for collecting a sample, analyzing a portion of the sample and shipping of an unadulterated remainder of the sample, said device comprising:

container means, having an opening, for collecting a sample, and a chamber, for storing said sample;

cap means for sealing the container means opening;

assay means, attached to said container means, for chemically analyzing said sample, said assay means being positioned on said container means for enabling direct visual observation thereof; and means, spaced apart from said chamber and said assay means, for introducing the sample portion into the assay means and preventing flooding of the assay means by the sample portion, said last mentioned means comprising a plenum disposed between said chamber sand said assay means and wick means, disposed between said plenum and said assay means, for providing fluid communication therebetween.

2. The assaying device according to claim 1 further comprising channel means for enabling the portion of said sample to enter said plenum upon inversion of said container means and means, responsive to rotation of the cap means, for releasably sealing the channel means from the chamber without unsealing the cap means from the container means.

3. The assaying device according to claim 2 further comprising means for preventing sample from entering the channel means during collection of the sample.

4. The assaying device according to claim 2 wherein said assay means comprises chromatograph means permanently attached to an exterior of a container means side wall.

5. The assaying device according to claim 4 wherein said channel means comprises means, defining at least one bore in the container means side wall, for conveying the sample to said chromatograph means.

6. The assaying device according to claim 1 wherein said means for sealing the channel means comprises a member depending from said cap means.

7. The assaying device according to claim 6 wherein the depending member is disposed on said cap means for sealing the channel means when the cap means is disposed on the container at a first angular position sealing the container and not sealing the channel means when the cap means is disposed on the container at a second angular position sealing the container.

8. The assaying device according to claim 1 wherein said assaying means comprises a plurality of separated thin layer chromatograph strips; each strip comprising means for chemically analyzing said sample for a different specific substance.

9. The assaying device according to claim 8 wherein said wick means is disposed for evenly distributing the sample portion to each of said plurality of separated thin layer chromatograph strips.

10. The assaying device according to claim 9 wherein said plurality of separated thin layer chromatograph strips is disposed in a generally parallel relationship with one another and with a longitudinal axis of the container means.

11. The assaying device according to claim 10 wherein said wick means is disposed at one end of each chromatograph strip and said chromatograph means further comprises pad means disposed at another end of each chromatograph strip for receiving fluid passing through the chromatograph strips.

12. An assaying device for collecting, analyzing and shipping of a sample, said device comprising:
   container means, having an opening, for collecting a sample, and a chamber, for storing said sample;
   cap means for sealing the container means opening;
   chromatograph means, attached to said container means, for chemically analyzing said sample, said chromatograph means being positioned on said container means for enabling direct visual observation thereof;
   means for introducing a portion of the sample within said chamber into said chromatograph means when said cap means is in a position sealing the container means opening; and
   means, spaced apart from said chamber and said assay means, for introducing the sample portion into the assay means and preventing flooding of the assay means by the sample portion, said last mentioned means comprising a plenum disposed between said chamber and said chromatograph means and wick, means, disposed between said plenum and said chromatograph means, for providing fluid communication therebetween.

13. The assaying device according to claim 12 further comprising means, responsive to rotation of the cap means, for releasably sealing the plenum from the chamber without unsealing the cap means from the container means.

14. The assaying device according to claim 13 further comprising means for directing the sample into the plenum only when the container means is inverted.

15. The assaying device according to claim 14 wherein said chromatograph means is permanently attached to an exterior of a container means side wall.

16. The drug screening device according to claim 13 wherein said wick means is disposed at one end of each chromatograph strip and said chromatograph means further comprises pad means disposed at another end of each chromatograph strip for receiving fluid passing through the chromatograph strips.

17. The drug screening device according to claim 12 wherein said means for sealing the plenum comprises a member depending from said cap means.

18. The drug screening device according to claim 17 wherein the depending member is disposed on said cap means for sealing the plenum when the cap means is disposed on the container at a first angular position sealing the container and not sealing the channel means when the cap means is disposed on the container at a second angular position sealing the container.

19. The drug screening device according to claim 15 wherein said chromatograph means comprises a plurality of separated thin layer chromatograph strips; each strip comprising means for chemically analyzing said body fluid for a different specific analyte.

20. The drug screening device according to claim 19 wherein said plurality of separated thin layer chromatograph strips is disposed in a generally parallel relationship with one another and with a longitudinal axis of the container means.

21. The drug screening device according to claim 20 wherein said wick means is disposed at one end of each chromatograph strip and said chromatograph means further comprises pad means disposed at another end of each chromatograph strip for receiving fluid passing through the chromatograph strips.

22. The drug screening device according to claim 17 further comprising means, defining at least one bore in the container means side wall, for conveying body fluid from said plenum to said chromatograph means through said wick.

23. A drug screening device for collecting a fluid sample, assaying a portion of the fluid sample, and shipping an unadulterated remainder of the fluid sample, said drug screening device comprising:
   containing means for collecting and storing of said fluid sample;
   cap means for sealing the container means; assay means, attached to said container means, for chemically analyzing a portion of said sample;
   means for enabling the sample portion to enter the assay means and prevent return of any of the sample portion to return to a remainder of the fluid sample in the container means; and
   means, spaced apart from said chamber and said assay means, for introducing the sample portion into the assay means and preventing flooding of the assay means by the sample portion, said last mentioned means comprising a plenum disposed between said chamber and said assay means and wick means, disposed between said plenum and said assay means, for providing fluid communication therebetween.

* * * * *